United States Patent [19]

McGahren et al.

[11] Patent Number: 4,996,305

[45] Date of Patent: * Feb. 26, 1991

[54] PROCESS FOR PRODUCING THE ANTIBIOTIC AND ANTITUMOR AGENTS LL-E33288ϵ-I AND LL-E33288ϵ-BR

[75] Inventors: William J. McGahren, Demarest, N.J.; George A. Ellestad, Pearl River, N.Y.

[73] Assignee: American Cyanamid Company, Stamford, Conn.

[*] Notice: The portion of the term of this patent subsequent to Dec. 18, 2007, has been disclaimed.

[21] Appl. No.: 161,625

[22] Filed: Feb. 29, 1988

[51] Int. Cl.$^5$ .................. C07H 15/00; C07H 1/00
[52] U.S. Cl. ................... 536/17.5; 536/4.1; 536/16.8; 536/16.9; 536/17.6; 536/18.4; 536/18.1; 536/17.2; 536/55.3; 536/122
[58] Field of Search ............... 536/16.8, 16.9, 17.5, 536/17.6, 18.4, 122, 18.1, 17.2, 55.3, 4.1

[56] References Cited

U.S. PATENT DOCUMENTS

| | | | |
|---|---|---|---|
| 4,539,203 | 9/1985 | Brankiewicz et al. | 424/117 |
| 4,554,162 | 11/1985 | Young et al. | 424/117 |
| 4,837,206 | 6/1989 | Golik | 514/25 |

FOREIGN PATENT DOCUMENTS

| | | |
|---|---|---|
| 0132082 | 1/1985 | European Pat. Off. |
| 0182152 | 5/1986 | European Pat. Off. |
| 2141425 | 12/1984 | United Kingdom |

OTHER PUBLICATIONS

Bunge et al; J. Antibiotics, 37(12):1566–1571 (1984).
Iwami et al; J. Antibiotics, 38(7):835–839 (1985).
Kiyoto et al; J. Antibiotics, 38(7):840–848 (1985).
Konishi et al; J. Antibiotics, 38(11):1605–1609 (1985).
Fry et al; Investigational New Drugs, 4:3–10 (1986).
Lee et al; J. Am. Chem. Soc., 109:3464–3466 (1987).
Schreiber et al; J. Am. Chem. Soc., 110:631–633 (1988).

*Primary Examiner*—Ronald W. Griffin
*Assistant Examiner*—Nancy S. Carson
*Attorney, Agent, or Firm*—Thomas S. Szatkowski

[57] ABSTRACT

Processes for producing antibacterial and anti-tumor agents designated LL-E33288ϵ-I and LL-E33288ϵ-Br using triphenylphosphine or a sulfhydryl-containing reagent are disclosed. Processes for producing reductively aromatized derivatives of other antibiotics are also disclosed.

8 Claims, No Drawings

PROCESS FOR PRODUCING THE ANTIBIOTIC AND ANTITUMOR AGENTS LL-E33288ε-I AND LL-E33288ε-BR

BACKGROUND OF THE INVENTION

The family of antibacterial and antitumor agents, known collectively as the LL-E33288 complex, are described and claimed in a series of related, commonly assigned U. S. patent applications, namely Ser. No. 672,031, filed Nov. 16, 1984 (now abandoned); Ser. No. 787,066, filed Oct. 17, 1985; and Ser. No. 9,321, filed Jan. 30, 1987.

These applications describe the LL-E33288 complex, the components thereof, namely LL-E33288$\alpha_1$-Br, LL-E33288$\alpha_1$-I, LL-E33288$\alpha_2$-I, LL-E33288$\alpha_2$-I, LL-E33288$\alpha_3$-Br, LL-E33288$\alpha_3$-I, LL-E33288$\alpha_4$-Br, LL-E33288$\beta_1$-Br, LL-E33288$\beta_1$-I, LL-E33288$\beta_2$-Br, LL-E33288$\beta_2$-I, LL-E33288$\gamma_1$-Br, LL-E33288$\gamma_1$-I, and LL-E33288$\delta_1$-I, and methods for their production by aerobic fermentation utilizing a new strain of *Micromonospora echinospora* ssp *calichensis* or natural or derived mutants thereof.

The antibacterial and antitumor agents LL-E33288ε-I and LL-E33288ε-Br, which are the subject of commonly assigned, copending Ser. No. 07/161,627, filed Feb. 29, 1988, are produced by the same microorganisms under same fermentation conditions. Ser. No. 07/161,627 describes methods for the production of LL-E33288ε-I and LL-E33288ε-Br as well as establishing their antibacterial and antitumor activity characterizing the products by physical and chemical data and disclosing a proposed structure.

Certain other antibiotics are pertinent to this invention, namely:

(1) Esperamicin BBM-1675, a novel class of potent antitumor antibiotics I. Physico-chemical data and partial structure. M. Konishi, et al., J. Antibiotics, 38, 1605 (1985). A new antitumor antibiotic comples. M. Konishi, et al., UK patent application GB No. 2,141,425A, May 15, 1985.

(2) New antitumor antibiotics, FR-900405 and FR-900406. I. Taxonomy of the producing strain. M. Iwami, et al., J. Antibiotics, 38, 835 (1985). New antitumor antibiotics FR-900405 and FR-900406. II. Production, isolation, characterization and antitumor activity. S. Kiyoto, et al., J. Antibiotics, 38, 840 (1985).

(3) PD 114759 and PD 115028, novel antitumor antibiotics with phenomenal potency. I Isolation and characterization. R. R. Bunge, et al., J. Antibiotics, 37, 1566 (1984). Biological and biochemical activities of the novel antitumor antibiotic PD 114759 and related derivatives. D. W. Fry, et al., Investigational New Drugs, 4, 3 (1986).

(4) New antibiotic complex CL-1577A and CL-1577B produced by *Streptomyces* sp. ATCC 39363. European Patent application No. 0,132,082,A2.

(5) CL-1577D and CL-1577E Antibiotic antitumor compounds, their production and use. U.S. Pat. No. 4,539,203.

(6) CL-1724 Antibiotic compounds, their production and use. U.S. Pat. No. 4,554,162.

SUMMARY OF THE INVENTION

It has now been discovered that antibacterial and antitumor agents LL-E33288ε-I and LL-E33288ε-Br may be synthetically derived by reductive aromatization of the corresponding iodo or bromo LL-E33288$\gamma_1$ derivative with a reagent such as triphenylphosphine, $\beta$-mercaptoethanol, reduced glutathione, 1,4-dithiothreitol or a variety of other sulfhydryl-containing reagents in a solvent such as dichloromethane, acetonitrile, ethyl acetate, methanol, ethanol or chloroform. The yield and product depend to a considerable degree on the polarity of the reagent and solvent. In addition, increasing the polarity of the reagent serves to increase the speed of the reaction. In a preferred embodiment, 1-4-dithiothreitol is the reagent and acetonitrile is the solvent.

It has further been determined that treatment of the aforementioned antibiotics LL-E33288$\alpha_1$-Br, LL-E33288$\alpha_1$-I, LL-33288$\alpha_2$-Br, LL-33288$\alpha_2$-I, LL-33288$\alpha_3$-Br, LL-E33288$\alpha_3$-I, LL-E33288$\alpha_4$-Br, LL-33288$\beta_1$-Br, LL-E33288$\beta_1$-I, LL-E33288$\beta_2$-Br, LL-E33288$\beta_2$-I and LL-E33288$\delta_1$-I, with the above reagents results in the production of the corresponding reductively aromatized antibiotic.

It has further been determined that treatment of the aforementioned antibiotics BBM-1675, FR-900405, FR-900406, PD 114759, PD 115028, CL-1577A, CL-1577B, CL-1577D, CLE-1577E and CL-1724, with the above reagents results in the production of the corresponding reductively aromatized antibiotic.

While the structures of LL-E33288 components have not been fully elucidated, proposed structures are given below to illustrate the reaction scheme.

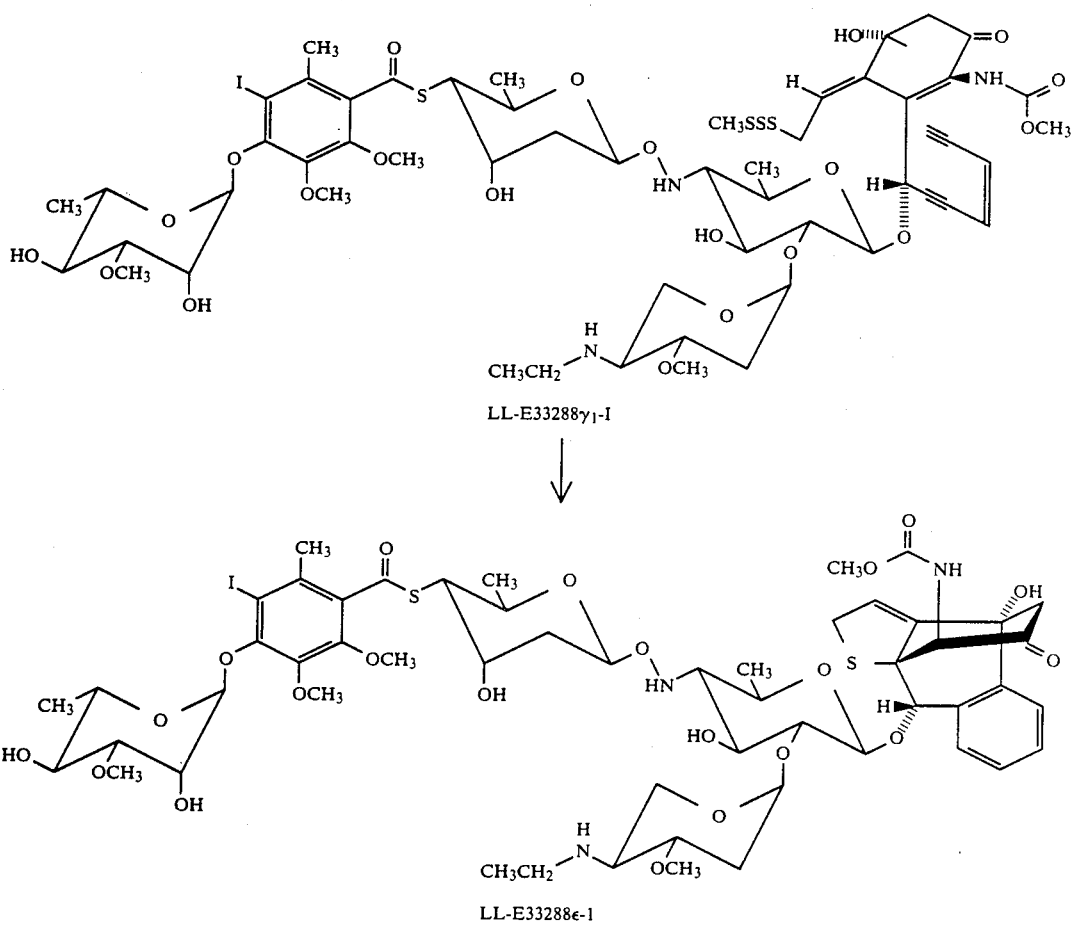

LL-E33288ε-1

The invention is further illustrated by the Examples set forth below which are not intended to limit the invention.

EXAMPLE 1

Preparation of LL-E33288ε-I by Treatment of LL-E33288γ₁-I with Triphenylphosohine A solution of 1.67 g of LL-E33288γ₁-I in 100 ml of dichloromethane was treated with a solution of 500 mg of triphenylphosphine in 5 ml of dichloromethane. This mixture was stirred for 2 hours and then filtered. The filtrate was taken to dryness, the residue dissolved in methanol and treated with 268 mg of triphenylphosphine with warming to effect solution. The reaction was then stirred for 16 hours at room temperature and filtered. The filtrate was evaporated to dryness and then chromatographed on a 60×3 cm (LH-20; pharmacia) column, eluting with hexane:dichloromethane:methanol (2:1:1). The fractions containing LL-E33288ε-I were combined providing 336 mg of partially purified product which was then rechromatographed on the same column. Fractions containing LL-E33288ε-I were identified using thin layer chromatography ("TLC"). The TLC plates were placed in ethyl acetate saturated with a buffer of 0.2M dipotassium hydrogen phosphate containing 10% isopropanol. The plates were then ultraviolet quenched to identify the fractions of interest(-fractions 11-15). Fractions 11-15 (5 ml each) were combined, concentrated to dryness and taken up in a small amount of ethyl acetate. This was added dropwise to an excess of stirred hexane and the precipitate collected, giving 112 mg. A 100 mg portion was then chromatographed on a preparative reverse phase high performance liquid chromatography column, eluting with acetonitrile:0.2M ammonium acetate buffer (37:63). The active fractions were identified based on their retention times on the column. The LL-E33288ε fractions were combined, the acetonitrile evaporated, the active component extracted into ethyl acetate and precipitated with hexane, giving 20 mg of pure LL-E33288ε-I. The identity of the product was confirmed by comparison with the product obtained from natural sources as described in Ser. No. 07/161,627.

EXAMPLE 2

Preparation of LL-E33288ε-Br by Treatment of LL-E33288γ-Br with Triphenylphosphine A portion of LL-E332887γ₁-Br is reacted following the procedure described in Example 1, giving LL-E33288ε-Br.

EXAMPLE 3

Preparation of LL-E33288ε-I by Treatment of LL-E33288γ₁-I with Dithiothreitol

A solution of 100 mg of LL-E33288γ₁-I in 8 ml of acetonitrile was treated with 59 mg of 1,4-dithiothreitol. The mixture was stirred for 3 hours and then filtered. The filtrate was concentrated to dryness, taken up in dichloromethane containing a small amount of methanol and chromatographed on silica gel, eluting successively with 2, 4 and 5% methanol in dichloromethane. Fractions 7, 8 and 9 were combined and evaporated. The residue was precipitated from hexane/ethyl acetate, giving 30 mg of pure LL-E33288ε-I.

EXAMPLE 4

Preparation of LL-E33288ε-Br by Treatment of LL-E33288γ₁-Br with Dithiothreitol

A portion of LL-E33288γ₁-Br is reacted following the procedure described in Example 3, giving LL-E33288ε-Br.

We claim:

1. A process for producing the antibacterial agent LL-E33288ε-I, having the structure:

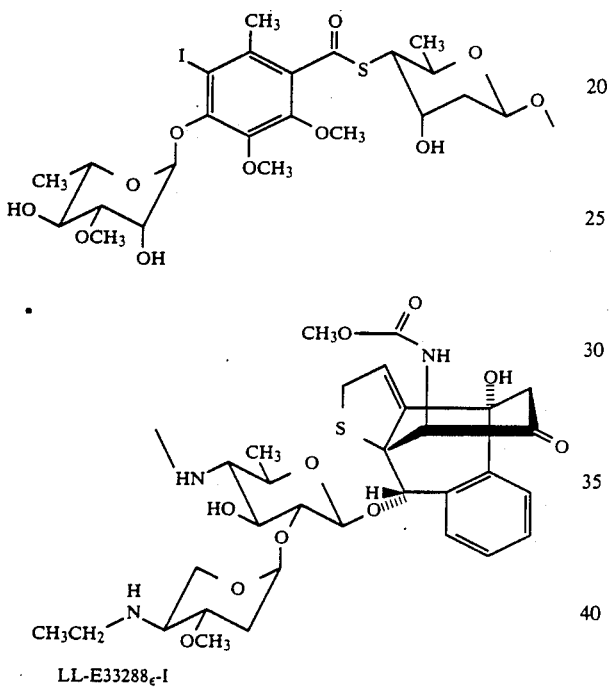

LL-E33288ε-I which comprises reacting LL-E33288γ₁-I having the structure:

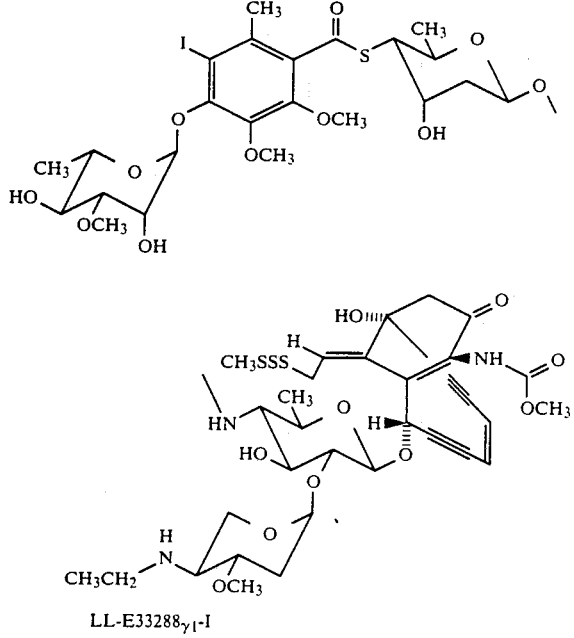

LL-E33288γ₁-I with triphenylphosphine or a sulfhydryl-containing reagent in a solvent, followed by chromatographic separation and purification of the LL-E33288ε-I.

2. The process of claim 1, wherein the sulfhydryl-containing reagent is selected from the group consisting of β-mercaptoethanol, reduced glutathione or 1,4-dithiothreitol and the solvent is selected from the group consisting of dichloramethane, acetonitrile, ethyl acetate, methanol, ethanol or chloroform.

3. The process of claim 2 wherein LL-E33288γ₁-I is reacted with triphenylphosphine in dichloromethane.

4. The process of claim 2 wherein LL-E33288γ₁-I is reacted with 1,4-dithiothreitol in acetonitrile.

5. A process for producing the antibacterial agent LL-E33288ε-Br having the structure:

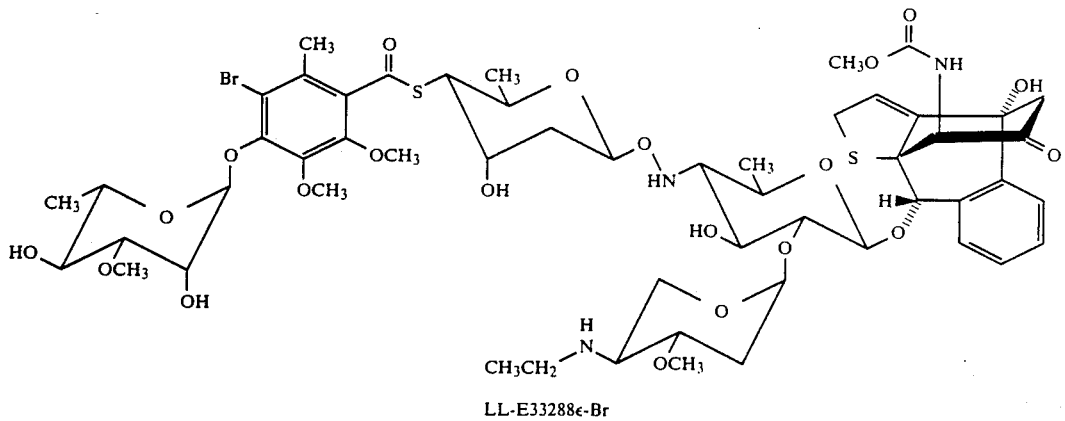

LL-E33288ε-Br which comprises reacting LL-E33288γ₁-Br having the structure:

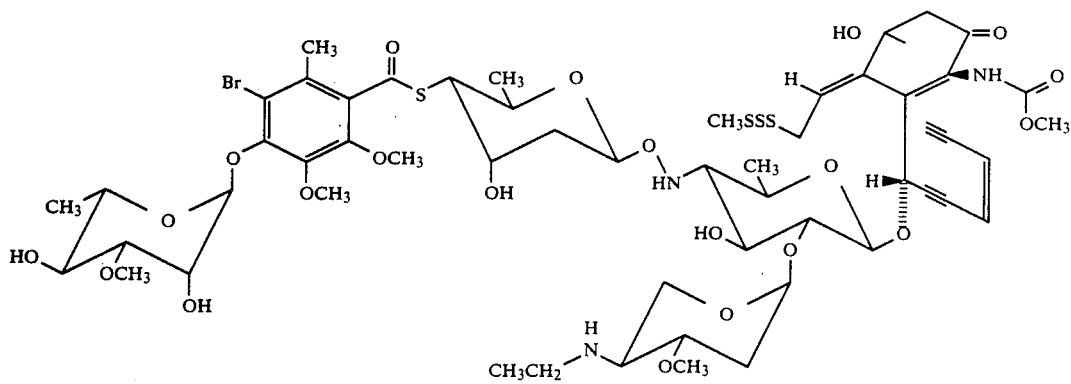

LL-E33288γ₁-Br with triphenylphosphine or a sulfhydryl-containing reagent in a solvent, followed by chromatographic separation and purification of the LL-E33288ε-Br.

6. The process of claim 5, wherein the sulfhydryl-containing reagent is selected from the group consisting of β-mercaptoethanol, reduced glutathione or 1,4-dithiothreitol and the solvent is selected from the group consisting of dichloromethane, acetonitrile, ethyl acetate, methanol, ethanol or chloroform.

7. The process of claim 6 wherein LL-E33288γ₁-Br is reacted with triphenylphosphine in dichloromethane.

8. The process of claim 6 wherein LL-E33288γ₁-Br is reacted with 1,4-dithiothreitol in acetonitrile.

* * * * *